(12) United States Patent
Uzarama et al.

(10) Patent No.: US 10,813,898 B2
(45) Date of Patent: Oct. 27, 2020

(54) SOLID DOSAGE FORMS OF VIGABATRIN

(71) Applicant: Orphelia Pharma, Paris (FR)

(72) Inventors: Charles Uzarama, Laval (CA); Patrick Gosselin, Laval (CA); Marie-Pierre Flament, Phalempin (FR)

(73) Assignee: Orphelia Pharma, Paris (FR)

( * ) Notice: Subject to any disclaimer, the term of this patent is extended or adjusted under 35 U.S.C. 154(b) by 0 days.

(21) Appl. No.: 16/081,926

(22) PCT Filed: Mar. 10, 2016

(86) PCT No.: PCT/IB2016/000436
§ 371 (c)(1),
(2) Date: Sep. 3, 2018

(87) PCT Pub. No.: WO2017/153800
PCT Pub. Date: Sep. 14, 2017

(65) Prior Publication Data
US 2019/0070138 A1    Mar. 7, 2019

(51) Int. Cl.
  *A61K 31/197* (2006.01)
  *A61K 9/20* (2006.01)
  *A61P 25/08* (2006.01)

(52) U.S. Cl.
  CPC .......... *A61K 31/197* (2013.01); *A61K 9/2018* (2013.01); *A61K 9/2027* (2013.01); *A61P 25/08* (2018.01); *A61K 9/2054* (2013.01); *A61K 9/2072* (2013.01)

(58) Field of Classification Search
  None
  See application file for complete search history.

(56) References Cited

U.S. PATENT DOCUMENTS

| 2006/0128696 | A1  | 6/2006  | Vezzani et al.         |
|--------------|-----|---------|------------------------|
| 2013/0078290 | A1* | 3/2013  | Pilgaonkar ...... A61K 9/0065 424/400 |
| 2013/0274348 | A1* | 10/2013 | Sato ............. A61K 9/0056 514/772.4 |

FOREIGN PATENT DOCUMENTS

| EP | 1927348 | 6/2008 |
| WO | WO 00/10554 | 3/2000 |
| WO | WO 2017/153800 | 9/2017 |

OTHER PUBLICATIONS

Elterman, R. D., et al. "Randomized trial of vigabatrin in patients with infantile spasms." Neurology 57.8 (2001): 1416-1421.*
Dimova, Petia S., and Rudolf Korinthenberg. "Efficacy of lamotrigine and vigabatrin in drug-resistant epilepsies of childhood." Pediatric neurology 21.5 (1999): 802-807.*
International Search Report and the Written Opinion dated May 20, 2016 From the International Searching Authority Re. Application No. PCT/IB2016/000436. (10 Pages).
Eke et al. "Severe Persistent Visual Field Constriction Associated With Vigabatrin", BMJ, 314(7075): 180-181, Jan. 18, 1997.
EMEA "Opinion of the Committee for Proprietary Medicinal Products Pursuant to Article 12 of Council Directive 75/319/EEC as Amended, for Vigabatrin", The European Agency for the Evaluation of Medicinal Products, Evaluation of Medicines for Human Use, EMEA, CPMP/1357/99-EN, p. 1-26, 1999.
French et al. "A Double-Blind, Placebo-Controlled Study of Vigabatrin Three G/Day in Patients With Uncontrolled Complex Partial Seizures", Neurology, 46(1): 54-61, Jan. 1996.
Gidal et al. "Vigabatrin: A Novel Therapy for Seizure Disorders", The Annals of Pharmacotherapy, 33912): 1277-1286, Dec. 1999.

* cited by examiner

*Primary Examiner* — John Pak
*Assistant Examiner* — Daniel L Branson

(57) ABSTRACT

The invention pertains to a solid dosage form comprising vigabatrin; a superdisintegrant, advantageously chosen from the list consisting of crospovidone, a cellulose derivative and a starch derivative; a non-reducing sugar, advantageously chosen from the list consisting of mannitol, xylitol, and sorbitol; and a stearate derivative, advantageously a stearate or stearyl fumarate salt, more advantageously sodium stearyl fumarate or magnesium stearate.

14 Claims, No Drawings

SOLID DOSAGE FORMS OF VIGABATRIN

RELATED APPLICATION

This application is a National Phase of PCT Patent Application No. PCT/IB2016/000436 having International filing date of Mar. 10, 2016. The contents of the above application are all incorporated by reference as if fully set forth herein in its entirety.

FIELD AND BACKGROUND OF THE INVENTION

The invention relates to a solid dosage form of vigabatrin adapted to the pediatric population. The solid dosage form of the invention comprises a specific selection of excipients, and is highly concentrated in the active principle, i.e. vigabatrin.

Epilepsy affects 1% of the world population and can in some instances be lethal. Early epilepsy onset carries a high risk of mental retardation and pharmacoresistance.

Vigabatrin (also known as gamma-vinyl-aminobutyric acid), first introduced in 1989 in the United Kingdom, was widely prescribed for the treatment of various forms of epilepsy (French et al., 1996; Gidal et al., 1999; Ben-Menachem et al., 2008), until vigabatrin-induced visual loss was first described in 1997 (Eke et al., 1997).

In 1999, 10 years after initial marketing authorization in the UK, a special safety review conducted by the European Medicines Agency (EMEA) under Article 12 of the European Commission Directive 75/319/EEC concluded that the benefit/risk ratio for vigabatrin remained favorable for two indications: first, as adjunctive therapy for patients with resistant partial onset seizures (POS) who had not responded to alternate therapy and second, as monotherapy in patients with infantile spasms (IS) (EMEA, CPMP/1357/99, 1999).

The recommended dosage of vigabatrin for adults and children 10 years of age and older (POS patients) is of 3 g/day (1.5 g twice daily), by oral administration with or without food. It is recommended that therapy be initiated at 1 g/day (500 mg twice daily), and further increased in 500 mg increments at weekly intervals depending on the response of the subject. It is currently manufactured and commercialized under the name Sabril®, as dosage forms being adapted to this recommended use, that is to say as film-coated tablets and granular powder for oral solution in packets both of 500 mg vigabatrin. Sabril® granular powder comprises povidone K30 (E1201) as excipient. Sabril® tablets comprise, as excipients, povidone K30 (E1201), microcrystalline cellulose (E460), magnesium stearate, sodium starch glycolate (Type A), hypromellose 15 mPa·s (E464), titanium dioxide (E171), macrogol 8000.

For infants with POS, the recommended starting dose of vigabatrin is 40 mg/kg/day twice daily. For infants with infantile spasms, the recommended starting dose of vigabatrin is 50 mg/kg/day. In clinical practice, doses up to 100 mg/kg/day can be prescribed.

However, there is currently no available dosage form adapted to the pediatric population.

Due to the large size of the 500 mg Sabril® tablets, they are not suitable for children under the age of 6 years.

Thus, only the granule for oral solution form is currently used for children. In the current medical practice, parents of infants with IS or refractory POS are asked to dissolve the sachet (or sachets) in a small amount of water and dispense it to the child using a feeding bottle or a syringe. Preparation and administration of the appropriate dose to neonates and young infants is challenging when small doses are required (below 500 mg), and thus fractions of the 500 mg sachet are needed.

This situation holds the risk of inadequate dosing. Under-dosing may result in poor seizure control with potential important consequences for the diseased children, especially in a severe condition as IS. Over-dosing could lead to potential side-effects. If the infants are repeatedly over-dosed, the cumulative exposure to vigabatrin will increase, consequently increasing the risk of visual field defects.

In addition, and as specified in the Summary of Product Characteristics, Sabril® granule sachets do not allow the preparation of concentrated solutions, the recommended vigabatrin concentration being of 50 mg/ml. Hence, using Sabril® granules, the administration of 500 mg vigabatrin to a child weighting about 10 kg requires dissolving the granules into 10 mL of water. However, and as recommended by the EMEA, the total liquid volume of medicine to be administered to children should not be above 5 mL or even 2-3 mL for infants (children under 2 years), in order to avoid regurgitation.

Hence, the current use of Sabril® granule for children remains inconvenient and possibly harmful.

Therefore there is a need for dosage forms of vigabatrin which are adapted to the treatment of the pediatric population. Because solid dosage forms of vigabatrin are more stable and easier to handle than liquid forms (as disclosed in the British pharmacopoeia), they are usually preferred. However, in the particular case of the pediatric use, an adapted dosage form would be expected to simplify dosing manipulation, that is to say enable administration of small doses. In addition, an appropriate dosage form of vigabatrin for the infant patients should disintegrate rapidly, in a small amount of water, as the volume of liquid that can be administered to infants is limited.

Therefore, the ideal specifications of a solid dosage form of vigabatrin appropriate for children and infants would be a dispersible tablet, which allows:
  a low dose increment,
  a quick dissolving in water,
  the preparation of concentrated aqueous solutions (e.g. 100 or 200 mg/mL).

However, this solution is not readily feasible because the active principle vigabatrin does not dissolve quickly in water. In addition, powdered vigabatrin is not easily compressible, and thus not suitable to make dispersible tablets.

Moreover, an adapted dosage form should contain a minimal amount and number of excipients. Indeed, although excipients are generally considered as pharmacologically inactive, they may still cause adverse effects. In addition, the excipients used should be considered as GRAS (Generally Recognized As Safe) substances for children and acceptable in terms of their taste, as children and infants are less likely than adults to accept bitter or unpleasant-tasting medication.

However, the formulation of solid dosage form comprising little and few excipients holds many difficulties, in particular in the case of vigabatrin which is difficult to compress. Indeed, to ensure correct dose administration and compliance, an adequate solid dosage form should suffer only little defects such as sticking, capping, or insufficient hardness.

"Sticking" is the term used when a small amount of material from a tablet is sticking to and being removed off from the tablet-surface by a punch face. Sticking is usually due to insufficient or improper lubrication. In terms of formulation, the technical remedy usually consists in the improvement of the lubrication.

"Capping" is the term used when the upper or lower segment of the tablet separates horizontally, either partially or completely from the main body of a tablet and comes off as a cap, during ejection from the tablet press, or during subsequent handling. Capping is usually due to air-entrapment in a compactor during compression, and subsequent expansion of tablet on ejection of a tablet from a die. In terms of formulation, the technical remedy usually consists in adding binder or changing the type of binder.

The hardness of tablets is the principle measure of mechanical strength, and is usually tested with tablet hardness tester. In practice, hardness of a solid dosage form corresponds to the crushing strength necessary to reach the breaking point (i.e. affecting the structural integrity of the solid dosage form). Hardness is closely linked to friability (i.e. its ability to remain whole "under conditions of storage, transportation, and handling before usage"). Insufficient hardness may depend on the overall chemical properties of the solid dosage form. In terms of formulation, the technical remedy usually consists in adding or modifying the amount and type of binding agent. Although insufficient hardness may also be compensated by appropriate manufacturing methods, such as increasing compression strength, this solution affects negatively the ability of the solid dosage form to disintegrate rapidly.

While those defects cannot be completely avoided, they should be minimized, to enable large scale manufacture. However, in this respect, excipients are often necessary in important amounts.

DESCRIPTION OF SPECIFIC EMBODIMENTS OF THE INVENTION

The invention solves the technical problem at hand by providing solid dosage forms of vigabatrin, comprising a specific selection of excipients.

The solid dosage form of the invention is highly concentrated in the active principle, in the present case in vigabatrin. As a consequence, the proportion of excipient is relatively low. In addition, the list of excipients comprised in the solid dosage form is limited to a few excipients known to be safe, in particular for the pediatric patients. Moreover, the selected excipients do not have a bad taste.

Despite its minimal formulation, the solid dosage form of the invention shows very little defects such as sticking, capping, or insufficient hardness.

Moreover, the solid dosage form of the invention disintegrates in water rapidly. It can be completely dissolved in a small volume of water to produce a water dispersion highly concentrated in active principle, which is easily administered to infants.

Importantly, the solid dosage forms of the invention can be prepared as small dosage forms of vigabatrin, so as to facilitate dosing when they are administered to the pediatric population. In other terms, the formulation used to prepare the solid dosage form of the invention may be used to produce dosage units of a small size, despite the technical issues usually met in this respect. Hence, the solid dosage forms of the invention are convenient to administrate low doses of vigabatrin. Additionally, the formulation of the solid dosage forms of the invention enables the preparation of scored tablets, which further facilitate accurate dosing. For instance, the solid dosage form may present in the form of scored tablets of 100 mg vigabatrin, thus allowing accurate 50 mg dosing steps.

The solid dosage form of the invention comprises vigabatrin, a superdisintegrant, a non-reducing sugar and a stearate derivative.

As shown in the experimental part, the inventors have surprisingly found that some of the excipients routinely used in pharmacy were improper for the preparation of solid dosage forms comprising a high concentration of vigabatrin.

Preferably, the solid dosage forms of the invention are devoid of at least one excipient chosen in the following list: microcrystalline cellulose, polyvinyl acetate, silicon dioxide and fructose. More preferably, the solid dosage forms of the invention are devoid of microcrystalline cellulose, polyvinyl acetate, silicon dioxide and fructose.

In the rest of the description, the quantity of the compounds is expressed as a percentage (%) by weight (w), i.e. the weight of the compound based on the weight of the solid dosage form.

By "vigabatrin" (CAS number: 60643-86-9), it is herein referred to (RS)-4-aminohex-5-enoic acid, of formula:

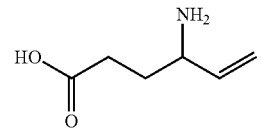

Vigabatrin is also known as gamma-vinyl-aminobutyric acid or gamma-vinyl-GABA. It is a structural analog of GABA which does not bind to GABA receptors.

Advantageously, in the solid dosage form of the invention, vigabatrin represents between 65 and 90%, preferably between 70 and 85%, more preferably between 75 and 80%, yet preferably between 78 and 80%, for example 78, 78.5, 79, 79.5 or 80% by weight.

Advantageously, the solid dosage form of the invention contains between 50 mg and 1000 mg vigabatrin per dosage form, preferably the solid dosage form contains 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg vigabatrin.

According to a specific embodiment, vigabatrin is provided as a powder. Advantageously, according to the invention, vigabatrin has a granulometry of less than or equal to 200 μm, more preferably less than or equal to 150 μm, 100 μm, 50 μm, 45 μm, 40 μm, 35 μm, 30 μm, 25 μm, 20 μm, 15 μm, 10 μm, or 5 μm.

It should be understood that according to the invention, the solid dosage form preferably comprises vigabatrin as the sole active ingredient, i.e. it does not contain any other active ingredient than vigabatrin. According to the invention, an "active ingredient" is herein defined as a pharmaceutically acceptable compound therapeutically effective in treating or preventing diseases and medical conditions, especially epilepsy.

The solid dosage form of the invention further comprises a superdisintegrant. The superdisintegrant is preferably chosen from the list consisting of crospovidone, cellulose derivatives, starch derivatives, and their mixtures. A preferred cellulose derivative is carboxymethylcellulose (CMC), for example sodium carboxymethylcellulose. A preferred starch derivative is starch glycolate, for example sodium starch glycolate. More preferably, the superdisintegrant is crospovidone.

By "crospovidone" (CAS number: 25249-54-1), it is herein referred to 1-ethenylpyrrolidin-2-one. Crospovidone is also known as polyvinylpolypyrrolidone, polyvinyl polypyrrolidone, PVPP, crospolividone or E1202. It is a highly cross-linked modification of polyvinylpyrrolidone.

By "sodium carboxymethylcellulose" (CAS number: 9004-32-4), it is herein referred to carboxymethyl cellulose sodium salt. Sodium carboxymethylcellulose is also known as carboxymethylcellulose sodium.

By "sodium starch glycolate" (CAS number: 9063-38-1), it is herein referred to carboxymethyl starch sodium salt. Sodium starch glycolate is also known as sodium carboxylmethyl starch.

Advantageously, in the solid dosage form of the invention, the superdisintegrant represents between 7 and 15%, preferably between 8 and 12%, more preferably between 9 and 10%, for example 9, 9.5 or 10% by weight.

The solid dosage form of the invention further comprises a non-reducing sugar. Preferably, the non-reducing sugar is chosen from the list consisting of xylitol, sorbitol, mannitol, and their mixtures. More preferably, the non-reducing sugar is mannitol.

By "xylitol" (CAS number: 87-99-0), it is herein referred to (2R,3R,4S)-pentane-1,2,3,4,5-pentanol. Xylitol is also known as pentahydroxypentane or D-Xylit.

By "sorbitol" (CAS number: 50-70-4), it is herein referred to (2S,3R,4R,5R)-hexane-1,2,3,4,5,6-hexol. Sorbitol is also known as D-glucitol, D-Sorbitol, Sorbogem or Sorbo.

By "mannitol" (CAS number: 69-65-8), it is herein referred to (2R,3R,4R,5R)-Hexan-1,2,3,4,5,6-hexol. Mannitol is also known as mannite or manna sugar.

The inventors have found that a minimal amount of non-reducing sugar is necessary to obtain solid dosage forms comprising a high concentration of vigabatrin.

Advantageously, in the solid dosage form of the invention, the non-reducing sugar represents at least 5% by weight.

More advantageously, in the solid dosage form of the invention, the non-reducing sugar represents between 7 and 15%, preferably between 8 and 12%, more preferably between 9 and 10%, for example 9, 9.5 or 10% by weight.

The solid dosage form of the invention further comprises a stearate derivative, advantageously a salt thereof. Preferably, the stearate derivative is a stearate or stearyl fumarate salt, more advantageously chosen from the list consisting of sodium stearyl fumarate, magnesium stearate, and their mixtures. This stearate derivative is used as a lubricant in the solid dosage form of the invention.

By "sodium stearyl fumarate" (CAS number: 4070-80-8), it is herein referred to sodium (E)-4-octadecoxy-4-oxobut-2-enoate. Sodium stearyl fumarate is also known as sodium octadecyl fumarate, sodium monostearyl fumarate, or sodium monooctadecyl fumarate.

By "magnesium stearate" it is herein referred to magnesium salts of fatty acids consisting essentially of stearic acid, and which may also comprise other fatty acids such as for instance palmitic acid in minor proportions. Preferably, the magnesium stearate according to the invention is the magnesium stearate of CAS number 557-04-0, i.e. magnesium salts of stearic acid. Magnesium stearate is a salt containing two equivalents of stearate (the anion of stearic acid) and one magnesium cation ($Mg^{2+}$).

Advantageously, in the solid dosage form of the invention, the stearate derivative represents at least 0.5%, preferably 1%, more preferably 1.25%, even more preferably 1.5% or 1.75% by weight. According to another embodiment, it does not exceed 2%. In other words, it can represent between 0.5 and 2%, preferably between 1 and 2%, more preferably between 1 and 1.75%.

The inventors have found that a proportion of stearate derivative equal or superior to 1.25% further limits the capping phenomenon. Advantageously, in the solid dosage form of the invention, the stearate derivative represents between 1.25 and 1.75%, for example 1.5% by weight.

In a preferred embodiment, the solid dosage form of the invention comprises vigabatrin, crospovidone, mannitol and a stearate derivative chosen from the list consisting of sodium stearyl fumarate, magnesium stearate and their mixtures.

In a specific embodiment, the solid dosage form of the invention consists of vigabatrin, crospovidone, mannitol and a stearate derivative chosen from the list consisting of sodium stearyl fumarate, magnesium stearate and their mixtures.

Because the solid dosage form of the invention aims at providing relatively small doses of vigabatrin, it is of particular interest that their formulation enables the production of small dosage forms, for instance dosage forms manufactured with small size punches. Yet, the manufacture of such small entities is particularly challenging, because small sized punches cannot bear great compression strength, which may result in insufficient hardness.

In this respect, the inventors have determined that when small sized punches are to be used, i.e. in particular when punches of a diameter equal or inferior to 7 mm are used, the use of sodium stearyl fumarate as a stearate derivative lessens the proportion of solid dosage forms showing capping phenomenon. Advantageously, in the solid dosage form of the invention, the stearate derivative is sodium stearyl fumarate.

Preferably, the solid dosage form of the invention comprises:
between 78 and 80% vigabatrin,
between 9 and 10% crospovidone,
between 9 and 10% mannitol,
between 1 and 2% sodium stearyl fumarate and/or magnesium stearate.

In a preferred embodiment, the solid dosage form of the invention comprises or consists of:
78.7% vigabatrin,
9.9% crospovidone,
9.9% mannitol, and
1.5% sodium stearyl fumarate and/or magnesium stearate, preferably sodium stearyl fumarate.

In another preferred embodiment, the solid dosage form of the invention comprises or consists of:
79.5% vigabatrin,
9.5% crospovidone,
9.5% mannitol, and
1.5% sodium stearyl fumarate or magnesium stearate, preferably sodium stearyl fumarate.

In a preferred embodiment the solid dosage form of the invention is devoid of at least one compound chosen in the list consisting of preservatives, antioxidants, coloring agents, flavoring agents and taste-masking agents. Preferably, the solid dosage form of the invention is devoid of preservatives and/or antioxidants. Preferably the solid dosage form of the invention is devoid of any preservatives, antioxidants, coloring agents, flavoring agents and taste-masking agents.

By "preservatives", it is herein referred to usual preservatives used in the preparation of pharmaceutical products, such as antimicrobial agents and chelating agents. Examples of preservatives include, but are not limited to, benzalkonium chloride, cetalokonium chloride, benzoates (e.g. sodium benzoates), benzyl alcohol, methyl paraben, propyl paraben, alkaly gallates, hydroxybenzoates and salts thereof (e.g. methyl or propyl hydroxybenzoates and salts thereof), phenyl mercuric salts (e.g. borates or nitrates), sodium hypochlorite, and acetic acid.

By "antioxidants", it is herein referred to usual antioxidants used in the preparation of pharmaceutical products, such as for instance ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives.

By "coloring agents", it is herein referred to usual coloring agents used in the preparation of pharmaceutical products, such as for instance: iron oxides, beta-carotene, indigotine, yellow orange S, tartrazine, Eriosky blue, titanium dioxide, quinoleine yellow, allura red, chlorophylline, sunset yellow.

By "flavoring agents", it is herein referred to usual flavoring agents used in the preparation of pharmaceutical products, such as for instance peppermint, menthol, cherry, orange, lemon, other acceptable fruit flavors, or their mixtures.

By "taste-masking agents", it is herein referred to usual taste-masking agents used in the preparation of pharmaceutical products, such as for instance water-soluble polymers used as taste-masking layers, sweeteners and effervescent agents. Examples of water-soluble polymers used as taste-masking layers include, but are not limited to, ethyl cellulose, polyvinyl acetate (PVA), cellulose acetate (CA), cellulose acetate butyrate (CAB), and methacrylate copolymers. Examples of sweeteners include, but are not limited to, sucralose and aspartame. Examples of effervescent agents include, but are not limited to sodium bicarbonate and citric acid.

In a specific embodiment and because of its preferred pediatric use, the solid dosage form may further comprise at least one coloring agent, flavoring agent and/or taste-masking agent.

According to another aspect, the solid dosage form of the invention is able to disintegrate rapidly in water, which facilitates its use.

Advantageously, the solid dosage form of the invention disintegrates in water at 37° C. in less than 1 minute, preferably less than 50 seconds, more preferably in less than 30 seconds.

According to the invention, the disintegration time is measured in usual experimental conditions. Such conditions are well known in the field of pharmacy, and are for instance thoroughly detailed in *The European Pharmacopoeia* (reference is made to paragraph 2.9.1). Briefly, the test is implemented using an apparatus consisting of a basket-rack assembly, a 1 L low-form beaker, a thermostatic arrangement for heating the fluid at the appropriate temperature, and a device for raising and lowering the basket in the immersion fluid at a constant frequency rate between 29 and 32 cycles per minute, through a distance of 50 mm to 60 mm. The volume of the fluid in the vessel is such that at the highest point of the upward stroke the wire mesh remains at least 15 mm below the surface of the fluid and descends to not less than 25 mm from the bottom of the vessel on the downward stroke.

The test is realized by:
placing one dosage unit in each of the six tubes of the basket, and possibly a disc;
operating the apparatus using water as the immersion fluid at the target temperature (for 37° C.: between 35 and 39° C.);
measuring the time necessary for complete disintegration.

Complete disintegration is defined as that state in which any residue of the unit, except fragments of insoluble coating or capsule shell, remaining on the screen of the test apparatus or adhering to the lower surface of the discs, if used, is a soft mass having no palpably firm core.

Moreover, the inventors have demonstrated that the solid dosage form of the invention can be rapidly dissolved at 20° C. in similar conditions.

Advantageously, the solid dosage form of the invention disintegrates in water at 20° C. in less than 3 minutes, preferably less than 1 minute, more preferably in less than 40 seconds.

In the context of the invention, it should be understood that this disintegration time is measured in a similar test as that defined above, but at 20° C.

While the usual methods to measure disintegration time detailed above may be valuable, they do not always reflect the behavior of a solid dosage form when the volume of water is limited. However, as already stressed, when a liquid solution is to be administered to an infant, and in particular in the case of pharmaceutical products (which may have a bitter taste), it is advantageous that the volume remains little.

Interestingly, the inventors have determined that the solid dosage form of the invention can be rapidly disintegrated in a small volume of water, as little as 5 ml, at room temperature, so as to prepare extemporaneous solutions of at least 100 mg/ml, preferably of 200 mg/ml vigabatrin. According to the invention, room temperature is defined as a temperature of between 19 and 25° C., preferably of about 25° C.

In the context of the invention, it should be understood that this disintegration time is measured by the following process. A defined number of solid dosage forms are introduced in a 20 ml beaker filled with 5 ml of purified water previously heated at 25° C. The mixture is shaked manually with a spatula until complete disintegration. The time necessary for complete disintegration is measured. The solid dosage form is considered completely disintegrated when there is no more agglomerate in solution, estimated by visual control.

Advantageously, the solid dosage form of the invention disintegrates in an appropriate amount of water necessary to produce solutions of 100 mg/ml, preferably 200 mg/ml vigabatrin, preferably at room temperature in less than 3 minutes, more preferably in less than 1 minute, yet preferably in less than 40 seconds. Typically, the volume of water can be 5 ml or even less.

According to the invention, the term "solid dosage forms" refers to solid compositions as tablets, granules, powders, beads, mini-tablets, and pellets. Preferably, the solid dosage form of the invention is a tablet or a pellet.

According to the invention, the term "tablets" encompasses compressed tablets and molded tablets, depending on the method of manufacture. Compressed tablets are obtained by compression, either dry compression or wet granulation followed by compression. Molded tablets are obtained by molding.

Tablets can be round, oblong, or unique in shape; thick or thin; large or small in diameter; flat or convex; unscored or scored in halves, thirds, or quadrants; engraved or imprinted with an identifying symbol and/or code number; coated or uncoated; colored or uncolored; one, two, or three layered. Preferably, when the solid dosage form is a tablet, it is a scored tablet, yet preferably a tablet scored in halves.

According to the invention, "pellets" can be defined as small, free-flowing, spherical particulates manufactured by the agglomeration of fine powders or granules of drug substances and excipients using appropriate techniques such as extrusion-spheronization.

The solid dosage forms of the invention can be prepared using routine techniques well known in the art. There are several well-known techniques for manufacturing compressed solid dosage forms: wet granulation followed by compression, double-compression (also known as dry granulation), direct compression and extrusion-spheronization.

These methods are well established and need not be extensively described. Briefly, their respective implementations may be summarized as follows.

In each of these methods, blending steps promote agglomeration of fine particles of the active principle into larger, less rapidly dissolving particles.

In the direct compression method, the drug and any other ingredients are blended together and directly compressed into the final tablet.

In the wet granulation method, pre-weighed drug and the excipients are blended. The blend is then mixed with a liquid such as water or ethanol which causes the particles to agglomerate into a damp mass. The damp mass is screened to produce granules which are then dried. The dry granules are screened to produce calibrated granules. Then, the granules are typically blended with a solid lubricant and possibly other ingredients. Lastly, the lubricated granules and any other extra-granular ingredients are compressed into a tablet.

In the double-compression method, the drug and the excipients are blended and then compressed in a first compression step. There are two conventional first compression techniques. One is roller compaction where the blend is fed between rollers which press it into sheets and the other is slugging where the blend is compressed into slugs, which are tablet-like forms that are typically larger than tablets intended for human consumption. The resulting sheets or slugs are then comminuted into granules, mixed with a solid lubricant and compressed in a second compression step to produce the final tablet.

In the extrusion-spheronization method, the drug and the excipients are dry blended. The method then implies wetting of the dry blend and extrusion of the wet mass through a screen to produce compacted cylindrical strands. The strands are broken into smaller segments which undergo smoothing and rounding to form round pellets in a spheronizer (which is essentially a device equipped with a grooved or serrated rotating disk). The round pellets are then dried.

The solid dosage forms of the invention are particularly appropriate for treating subjects with resistant partial onset seizures (POS) or with infantile spasms, in particular children under the age of 10 years, and especially infants. According to the invention, "infants" are children under the age of 2 years.

Another object of the invention is the solid dosage form of the invention for medical use, preferably for use in the treatment of resistant partial onset seizures (POS) or of infantile spasms in a subject. Advantageously, the subject is a child under the age of 10 years, more advantageously an infant.

Preferably, the solid dosage form of the invention is for use in the treatment of resistant partial onset seizures of a child under the age of 10 years, more advantageously an infant, and the daily dosage is of between 0.5 g and 3 g of vigabatrin.

Preferably, the solid dosage form of the invention is for use in the treatment of infantile spasms of a child under the age of 10 years, more advantageously an infant, and the daily dosage is of between 40 mg/kg of the subject and 150 mg/kg of the subject.

In a particular embodiment, the solid dosage form for medical use is administered orally, preferably in a liquid form after disintegration in water, preferably as a solution of at least 100 mg/ml vigabatrin, preferably around 200 mg/ml vigabatrin.

The solid dosage prepared as a solution may be administered with the help of a syringe. Embodiments of the invention are presented in the following examples, which are not intended as being limitative.

EXAMPLES

A. Determination of a Selection of Appropriate Excipients for Adequate Vigabatrin Solid Dosage Forms Preliminary experiments were made to determine the appropriate excipients enabling the production of solid dosage forms of vigabatrin comprising a high concentration in active principle. Among the criteria to consider adequacy were the physical properties of the solid forms obtained (hardness and capping), as well as disintegration time in water. Solid dosage forms with hardness below 1 kP, too much capping phenomenon or a disintegration time above one minute were considered inadequate.

Overview of the Experiments:

Mixtures of vigabatrin with various excipients were prepared.

Solid dosage forms were prepared using different usual techniques such as direct compression, wet granulation or extrusion/spheronization.

The properties of the solid dosage forms were determined: capping, hardness and disintegration time of said solid dosage forms were measured.

1. Methods a. Mixtures of Vigabatrin with Various Excipients

Different mixtures of vigabatrin with various excipients were made, to be used for the preparation of pellets or tablets. The excipients used are detailed below:

TABLE 1

| Excipients used and their compositions | |
|---|---|
| Product name | Ingredients |
| Vigabatrin | Vigabatrin |
| Prosolv ® ODT | Microcrystalline Cellulose, Colloidal Silicon Dioxide, Mannitol, Fructose, Crospovidone |
| Ludiflash ® | Mannitol Crospovidone Polyvinyl acetate |
| Pearlitol 160C | Mannitol |
| Tabulose-101 | Microcristalline cellulose, type 101 |
| Polyplasdone XL 10 | Crospovidone |
| LIGAMED MF-2-V | Magnesium stearate |
| Pruv | Sodium stearyl fumarate |

The formulations of the mixtures are presented in the table below. The quantities of product are indicated in percentage by weight based on the total weight of the mixture.

TABLE 2

Mixtures for the preparation of the solid dosage forms

| Product name | 001 | 003 | 004 | 004B | 005 | 006B | 007 |
|---|---|---|---|---|---|---|---|
| Vigabatrin | 80 | 80 | 80 | 79.2 | 65 | 75.125 | 79.2 |
| Prosolv ODT | 19 | 0 | 0 | 0 | 0 | 0 | 0 |
| Ludiflash | 0 | 19 | 0 | 0 | 0 | 0 | 0 |
| Pearlitol 160C | 0 | 0 | 10 | 9.9 | 0 | 10.325 | 9.9 |
| Tabulose-101 | 0 | 0 | 0 | 0 | 17.5 | 0 | 0 |
| Polyplasdone XL 10 | 0 | 0 | 10 | 9.9 | 17.5 | 13.625 | 9.9 |
| LIGAMED MF-2-V | 1 | 1 | 0 | 1 | 0 | 0.925 | 0 |
| Pruv | 0 | 0 | 0 | 0 | 0 | 0 | 1 | b. Preparation of the Solid Dosage Forms

Tablets and pellets were prepared using different techniques, such as direct compression, wet granulation, and extrusion/spheronization. Those techniques are routine in the field of pharmacology, and need not be thoroughly detailed herein.

Briefly, when direct compression was used, a dry blend of the products (except for the stearate or stearyl fumarate salt) was prepared. The mixture of products was then sieved over a mesh screen and premixed. The stearate or stearyl fumarate salt (when applicable) was sieved over a mesh screen added to this premix, and the resulting composition was mixed. The final mixture was then compressed using a hydraulic press.

When wet granulation was used, a dry premix of the products (except for the stearate or stearyl fumarate salt) was prepared with a low shear mixer/granulator. Water was then added to this first blend to produce a wet mass. The wet mass was granulated then dried, either in an oven or at room temperature to produce a dried mass (also called "dry granules"). When applicable, the stearate or stearyl fumarate salt was then added to the dry granules, and this mixture was mixed in a blender (V-blender), to produce a granule blend called "final granule blend". The final granule blend was then compressed using a hydraulic press.

When extrusion/spheronization was used, a dry premix of the products was prepared with a low shear mixer. Water was added to this dry mixture to produce a wet mass. The wet mass was then extruded and spheronized to produce pellets. The pellets were put to dry on a fluid bed.

c. Determination of the Properties of the Solid Dosage Forms

The properties of the obtained solid dosage forms were determined: capping, hardness and disintegration time of said solid dosage forms were measured.

Capping:

A sample of solid dosage form was used, which were submitted to compression testing. Compression testing was conducted using a Carver hydraulic hand press (model C, Carver, Menomonee Falls, Wis., USA) with 30 mm diameter round flat tooling and using a 6 stations rotary tablet press machine type PR6 (SVIAC, Antony, France) with 3.0 mm diameter round concave X-deep tooling strengths or with 2.0 mm diameter round concave X-deep tooling, depending of the strength of the solid dosage form.

After compression testing, the solid dosage forms showing capping were numbered.

Hardness:

Hardness values were determined via a diametral crushing test using a VK200 hardness tester unit model 40-2000 (VanKel Industries, Edison, N.J., USA) according to USP <1217>.

Disintegration:

The disintegration times of mini-tablets were determined in distilled water at 37° C. according to USP <701> method using a disintegration bath (model QC-21, Hanson Research, Chatsworth, Calif., USA). The disintegration time of pellets was evaluated using 900 ml of purified water heated at 37° C. under slow magnetic stirring on a heater/stirrer (RET basic) plate equipped with a thermostat (ETS-D4) (IICAO Werke GmbH & Co. KG, Staufen, Germany).

2. Results

Mixtures 001 did not enable the production of adequate solid dosage form. The solid dosage forms were extremely friable, as hardness was of between 0.5 and 0.9 kP, such that capping could not be measured. Consequently, disintegration time was not assayed.

Mixture 003 showed improved hardness compared to 001, of between 1.1 and 1.6 kP. However, capping was important. Disintegration time at 37° C. was of between 2 minutes 20 seconds and 2 minutes 24 seconds.

Mixture 004 showed improved hardness compared to 001 and 003, as it was of about 1.8 kP. Disintegration time was of between 20 seconds and 35 seconds. However, it could not be used in processes such as direct compression and wet granulation without the addition of a stearate or stearyl fumarate salt (the mixture would then be equivalent to mixture 004B). On the other hand, when used in extrusion/spheronisation process, the pellets could not be spheronized properly.

Mixture 004B showed good properties. Hardness was of between 1 and 2.7 kP, without significant capping phenomenon. Disintegration time was of between 14 seconds and 1 minute.

Mixture 005 could not be used for direct compression, nor wet granulation. The disintegration time was very long, of between 4 to 9 minutes. The formulation was discarded, hardness and capping were not measured.

Mixture 006B showed good properties. Hardness was of about 1.7 kP, without significant capping phenomenon. Disintegration time was of between 22 seconds and 28 seconds.

Mixture 007 showed properties similar to that of mixture 004B.

Conclusion

These results showed that the presence of a stearate derivative was mandatory in the initial formulation to obtain appropriate solid dosage forms. This is supported by the poor physical properties of solid dosage forms obtained from mixture 004, and the poor dissolution time of solid dosage forms obtained from mixture 005. Mixtures 004B and 007, particularly compared to mixture 004, demonstrate that the stearate derivative may either be magnesium stearate or sodium stearyl fumarate.

Moreover, while mixture 003 was improper for the production of solid dosage form having appropriate physical properties, mixture 004B gave very good results. The sole difference being the presence of polyvinyl acetate (in ludiflash), this excipient could be considered as inappropriate in solving the technical problem.

Similarly, when comparing the physical behavior of solid dosage forms prepared with mixture 001 and that of solid dosage forms prepared with mixture 006B, it appears that microcrystalline cellulose, colloidal silicon dioxide and fructose are not appropriate for obtaining solid dosage forms with the desired properties. This is further supported with the results obtained for solid dosage forms prepared with mixture 005.

Based on those preliminary results, only formulations 004B, 006B and 007, i.e. comprising vigabatrin, mannitol, crospovidone and either magnesium stearate or sodium stearyl fumarate enable the preparation of solid dosage forms with a high concentration of vigabatrin (between 75 and 80% w/w).

B. Optimization of the Formulation for the Preparation of Solid Dosage Forms of Small Size 1. Method Further experiments were made to evaluate the effect of variation of the relative weight of the excipients on the feasibility of the solid dosage forms. The formulations were used to prepare tablets of a size of about 7 mm diameter, comprising 100 mg vigabatrin. Capping of the tablets was assayed. Moreover, sticking was monitored during preparation of the solid dosage forms.

TABLE 3

Mixtures prepared for optimization of the solid dosage forms

| Product name | 004B | 004X | 006 | 006B | 007 | 007B |
|---|---|---|---|---|---|---|
| Vigabatrin | 79.2 | 79 | 80 | 75.125 | 79.2 | 78.7 |
| Pearlitol 160C | 9.9 | 9.875 | 4.5 | 10.325 | 9.9 | 9.9 |
| Polyplasdone XL 10 | 9.9 | 9.875 | 14.5 | 13.625 | 9.9 | 9.9 |
| LIGAMED MF-2-V | 1 | 1.25 | 1 | 0.925 | 0 | 0 |
| Pruv | 0 | 0 | 0 | 0 | 1 | 1.5 |

2. Results

Mixture 004B: when small tablets were prepared, using punches of a diameter of 7 mm, sticking was observed. This is probably due to the low compression strength used in this case. The resulting small tablets showed capping phenomenon.

Mixture 004X showed improved properties compared to 004B, since no sticking was observed when tablets were prepared using punches of a diameter of 7 mm. Some capping phenomenon was observed. Disintegration time was of 45 to 50 seconds.

Mixture 006 could not be compressed.

Mixture 007: when small tablets were prepared, using punches of a diameter of 7 mm, no sticking was observed. The resulting small tablets showed capping phenomenon.

Mixture 007B showed improved properties compared to 007, since no capping phenomenon was observed when tablets were prepared using punches of a diameter of 7 mm. Disintegration time was of about 45 seconds.

Conclusions

The results obtained for small solid dosage forms prepared with mixture 006, in comparison with those prepared with mixture 006B, show that a minimal amount of mannitol is necessary in the formulation, i.e. more than 4.5% by weight of the formulation (i.e. of the solid dosage form).

In the particular case of small dosage forms, the use of sodium stearyl fumarate as a stearate derivative shows improved properties (mixture 007) compared to similar formulations comprising magnesium stearate (mixture 004B).

Moreover, when the amount of the stearate derivative was equal or superior to 1.25%, no sticking was observed. When the amount of stearate derivative was about 1.5%, no capping was observed.

As demonstrated in experimental part A, those optimized conditions are not mandatory to the production of all vigabatrin solid dosage forms, since mixtures 004B and 007 previously gave good results in less challenging processes. However, they are beneficial in the particular case of small dosage forms.

C. Secability of the solid dosage form

1. Method

Tests were made to confirm that the solid dosage forms were compliant with the requirement of the European pharmacopoeia regarding secability. Scored tablets of 100 mg and 500 mg vigabatrin were prepared, using mixture 007B. 30 tablets of each dosage were spitted and weighted, to verify that the criteria of the European pharmacopoeia were met.

2. Results

The results are displayed in the table below:

TABLE 4 results of secability test

| | Mass of the entire solid dosage form | Mass of the first half (after splitting) | Mass of the second half (after splitting) |
|---|---|---|---|
| Average obtained for 30 tablets of 100 mg vigabatrin | 126.5 mg | 62.2 mg | 63.6 mg |
| Average obtained for 30 tablets of 500 mg vigabatrin | 635.93 mg | 326.93 mg | 306.68 mg |

In addition, it should be stressed that, for both 100 mg and 500 mg tablets, the mass of either the first or the second half of the dosage form were comprised with an interval of 85% to 115% of the average mass.

Both 100 mg and 500 mg vigabatrin satisfied the standards for secability according to the European pharmacopoeia.

Other Embodiments of the Solid Dosage Form

To assess whether the optimal conditions defined above could be extended to slightly different formulations, the following mixture (mixture 008) was prepared:
79.5% vigabatrin,
9.5% crospovidone,
9.5% mannitol, and
1.5% sodium stearyl fumarate.

Scored tablets of 100 mg and 500 mg vigabatrin were prepared using this mixture. No major defects were detected. The main technical features of the scored tablets are detailed in the tables below.

TABLE 5 technical features of vigabatrin scored tablets 100 mg (according to the invention)

| Controls | Reference | Specifications | Results |
|---|---|---|---|
| Appearance | Visual | White oval tablets with a vertical score on one side | White oval tablets with a vertical score on one side |

TABLE 5-continued technical features of vigabatrin scored tablets 100 mg (according to the invention)

| Controls | Reference | Specifications | Results |
|---|---|---|---|
| Mean mass | Ph. Eur. 2.9.5 | 127 mg +/− 5% = 120.7 to 133.4 mg | 127.8 mg |
| Uniformity of mass | Ph. Eur. 2.9.5 | On 20 unities: not more than 2 individual masses deviate from the average mass by more than 7.5% and none deviates by more than 15% | Compliant |
| Uniformity of mass of the subdivided parts | Tablets monograph | On 30 unities: not more than 1 individual mass is outside the limit of 85 percent to 115 percent of the average mass and no individual mass is outside the limit of 75 percent to 125 percent of the average mass. | Compliant |
| Friability | Ph. Eur. 2.9.7 | Loss of mass ≤ 1.0% | 0.22% |
| Disintegration in water (37° C.) | Ph. Eur. 2.9.1 | ≤1 min. | 16 sec. |
| Disintegration in water (20° C.) | Ph. Eur. 2.9.1 | ≤3 min. | 31 sec. |
| Hardness | Ph. Eur. 2.9.8 | For information | 38 Newton (min: 37; max: 41) |

TABLE 6 technical features of vigabatrin scored tablets 500 mg (according to the invention)

| Controls | Reference | Specifications | Results |
|---|---|---|---|
| Appearance | Visual | White oval tablets with a vertical score on one side | White oval tablets with a vertical score on one side |
| Mean mass | Ph. Eur. 2.9.5 | 635 mg +/− 5% = 603.3 to 666.8 mg | 645.5 mg |
| Uniformity of mass | Ph. Eur. 2.9.5 | On 20 unities: not more than 2 individual masses deviate from the average mass by more than 5% and none deviates by more than 10% | Compliant |
| Uniformity of mass of the subdivided parts | Tablets monograph | On 30 unities: not more than 1 individual mass is outside the limit of 85 percent to 115 percent of the average mass and no individual mass is outside the limit of 75 percent to 125 percent of the average mass. | Compliant |
| Friability | Ph. Eur. 2.9.7 | Loss of mass ≤ 1.0% | 0.48% |
| Disintegration in water (37° C.) | Ph. Eur. 2.9.1 | ≤1 min. | 16 sec. |
| Disintegration in water (20° C.) | Ph. Eur. 2.9.1 | ≤3 min. | 28 sec. |
| Hardness | Ph. Eur. 2.9.8 | For information | 37 Newton (min: 36; max: 39) |

Disintegration time was measured in water at 20° C. and 37° C. according to Ph. Eur. 2.9.1. The results are shown in the table below.

TABLE 7 disintegration of vigabatrin scored tablets (according to the invention)

| Test items | Batch # | Specifications | Time for disintegration |
|---|---|---|---|
| 100 mg solid dosage forms | 1008012277 (TGO-024) | ≤1 min. at 37° C. ≤3 min. at 20° C. | 16 sec. 31 sec |
| 500 mg solid dosage forms | 1008012278 (TGO-025) | ≤1 min. at 37° C. ≤3 min. at 20° C. | 16 sec. 28 sec. |

The solid dosage forms solubilize in less than 1 min and thus comply with the pharmacopoeia for orodispersible and soluble tablets, respectively.

Disintegration time was also measured under "clinical practice conditions". The vigabatrin dose to be disintegrated in 5 mL of water at room temperature was set at 1000 mg, corresponding to 2 scored tablets of 500 mg vigabatrin according to the invention. The disintegration times is measured by the following process. The number of solid dosage forms defined above (2 tablets) is introduced in a 20 ml beaker filled with 5 ml of purified water previously heated at 25° C. The mixture is shaken manually with a spatula until complete disintegration. The time necessary for complete disintegration is measured. The solid dosage form is considered completely disintegrated when there is no more agglomerate in solution, estimated by visual control.

Results are shown in the table below:

TABLE 8

Disintegration of vigabatrin dosage forms under clinical practice conditions

| Test items | Conditions | Time for disintegration |
|---|---|---|
| 2 × 500 mg solid dosage form according to the invention | Water (5 mL), 25° C. | 22 sec. |

CONCLUSIONS

The adequate physical properties of solid dosage forms prepared from mixtures 004B, 004X, 006B, 007 and 007B were also found to be present in solid dosage forms prepared with mixture 008. Indeed it was possible to prepare solid dosage forms comprising a high concentration of vigabatrin which showed no capping phenomenon, no sticking during manufacture, and had the desired disintegration time, i.e. inferior to 1 minute.

In addition, the mixture 008 was adequate for the preparation of smaller solid dosage forms, comprising 100 mg vigabatrin, with no sticking or capping phenomenon.

Importantly, the disintegration time of both 500 mg and 100 mg solid dosage forms according to the invention is very low, about 16 seconds at 37° C. and about 28 to 31 seconds at 20° C.

Finally, highly concentrated solutions of vigabatrin, i.e. having a concentration of 200 mg/ml vigabatrin, could be prepared with the solid dosage forms of the invention. These solutions are more concentrated than the 50 mg/ml vigabatrin solutions obtained with Sabril® granules (as recommended in the Summary of Product Characteristics of Sabril® sachets).

BIBLIOGRAPHY

French J A, Mosier M, Walker S, Sommerville K, Sussman N, *Neurology,* 1996, 46:54-61.
Gidal B E, Privitera M D, Sheth R D, Gilman J T, *Ann Pharmacother* 1999, 33:1277-1286.
Ben-Menachem E, O Dulac, C Chiron. Vigabatrin. *Epilepsy a comprehensive textbook*, P Engel Ed, 2nd edition, 2008, vol 3, chapt 161, pp 1683-1693.
Eke T, Talbot J F, Lawden M C, *BMJ,* 1997, 314:180-181.
The European Agency for the Evaluation of Medicinal Product, CPMP/1357/99-EN: Opinion of the committee for proprietary medicinal products pursuant to article 12 of council directive 75/319/EEC as amended, 1999.

What is claimed is:

1. Solid dosage form comprising:
vigabatrin;
crospovidone;
mannitol; and
sodium stearyl fumarate or magnesium stearate,
wherein vigabatrin represents between 65 and 85% by weight of the solid dosage form, crospovidone represents between 7 and 15% by weight of the solid dosage form, mannitol represents between 7 and 15% by weight of the solid dosage form, and the sodium stearyl fumarate or magnesium stearate represents between 0.5 and 2% by weight of the solid dosage form, and wherein the solid dosage form disintegrates in water at 20° C. in less than 3 minutes.

2. Solid dosage form according to claim 1, wherein it consists of vigabatrin, crospovidone, mannitol and sodium stearyl fumarate.

3. Solid dosage form according to claim 1, wherein vigabatrin represents between 70 and 85% by weight of the solid dosage form.

4. Solid dosage form according to claim 1, wherein the superdisintegrant represents between 8 and 12% by weight of the solid dosage form.

5. Solid dosage form according to claim 1, wherein the non-reducing sugar represents between 8 and 12% by weight of the solid dosage form.

6. Solid dosage form according to claim 1, wherein the stearate derivative represents between 1 and 2% by weight of the solid dosage form.

7. Solid dosage form according to claim 1, wherein it comprises between 50 mg and 1000 mg vigabratin per dosage form.

8. Solid dosage form according to claim 1, wherein it disintegrates in water at 37° C. in less than 1 minute.

9. Solid dosage form according to claim 1, wherein it is a tablet.

10. The solid dosage form as defined in claim 1 for medical use.

11. A method of treatment of resistant partial onset seizures or of infantile spasms in a subject under the age of 10 years, the method comprising disintegrating at least one solid dosage form in water to obtain a liquid form, and administering the liquid form orally to a subject in need thereof, thereby treating the resistant partial onset seizures or infantile spasms, wherein the solid dosage form comprises
vigabatrin;
crospovidone;
mannitol; and
sodium stearyl fumarate or magnesium stearate,
wherein vigabatrin represents between 65 and 85% by weight of the solid dosage form, crospovidone represents between 7 and 15% by weight of the solid dosage form, mannitol represents between 7 and 15% by weight of the solid dosage form, and the sodium stearyl fumarate or magnesium stearate represents between 0.5 and 2% by weight of the solid dosage form, and wherein the solid dosage form disintegrates in water at 20° C. in less than 3 minutes.

12. The method according to claim 11, wherein the subject is an infant.

13. The method according to claim 11, wherein the method is for the treatment of resistant partial onset seizures and the daily dosage is of between 0.5 g and 3 g of vigabatrin.

14. The method according to claim 11, wherein the method is for the treatment of infantile spasms and the daily dosage is of between 40 mg/kg and 150 mg/kg of the subject.

* * * * *